United States Patent
Bar-Haim et al.

(10) Patent No.: US 7,552,021 B2
(45) Date of Patent: Jun. 23, 2009

(54) DEVICE AND METHOD FOR IMPROVING HUMAN MOTOR FUNCTION

(75) Inventors: Simona Bar-Haim, Beer Yaakov (IL); Mark Belokopytov, Karnei Shomron (IL)

(73) Assignee: Step of Mind Ltd., Tel Aviv (IL)

( * ) Notice: Subject to any disclaimer, the term of this patent is extended or adjusted under 35 U.S.C. 154(b) by 0 days.

(21) Appl. No.: 11/861,316

(22) Filed: Sep. 26, 2007

(65) Prior Publication Data

US 2008/0134541 A1    Jun. 12, 2008

Related U.S. Application Data

(60) Provisional application No. 60/873,296, filed on Dec. 7, 2006.

(51) Int. Cl.
*G01C 25/00* (2006.01)
(52) U.S. Cl. .......................... 702/97; 602/36
(58) Field of Classification Search .................. 702/19, 702/33, 41, 79, 97, 154–155, 158, 160, 166; 473/217–218, 270–273; 602/1–3, 23, 25, 602/28–29, 36
See application file for complete search history.

(56) References Cited

U.S. PATENT DOCUMENTS

| | | | | |
|---|---|---|---|---|
| 5,049,079 A | * | 9/1991 | Furtado et al. | 434/253 |
| 5,676,218 A | * | 10/1997 | Hirose | 180/181 |
| 6,432,057 B1 | * | 8/2002 | Mazess et al. | 600/449 |
| 6,610,101 B2 | * | 8/2003 | Herr et al. | 623/24 |
| 6,684,531 B2 | * | 2/2004 | Rennex | 36/27 |
| 2004/0173220 A1 | | 9/2004 | Harry et al. | 128/892 |
| 2006/0130594 A1 | * | 6/2006 | Ikeuchi | 73/862.08 |
| 2006/0217233 A1 | * | 9/2006 | Lee | 482/9 |
| 2006/0249315 A1 | * | 11/2006 | Herr et al. | 180/8.1 |

OTHER PUBLICATIONS

S.J. Schiff, et al; "Controlling chaos in the brain" *Nature* 1994;370: 615-20.
A. Garfinkel et al. "Controlling cardiac chaos" *Science* 1992;257: 1230-5.
A.A Priplata et al; "Noise-enhanced balance control in patients with diabetes and patients with stroke" *Annals of Neurology* 2006;59: 4-12.

(Continued)

*Primary Examiner*—Eliseo Ramos Feliciano
*Assistant Examiner*—Mary C Baran
(74) *Attorney, Agent, or Firm*—Mark M. Friedman

(57) ABSTRACT

It is provided a system for improving locomotion of a human user, by changing an inclination or height of a stance surface of a device for donning on a leg during walking. The system includes a device, a sensor and a microprocessor. The device includes a platform which securely receives the shoe or foot of the user, a sole and mechanisms between the platform and the sole. Each mechanism has a motor and a thrusting element which changes the height of the platform relative to the sole. The sensor is associated with the lower limb, it senses the locomotion of the user and issues a corresponding data signal to the microprocessor. The microprocessor processes the locomotion information, determines the locomotion phase, and controls the mechanisms to effect changing of the inclination and/or the height of the stance surface during a swing phase. Also, the microprocessor introduces random changes thereof.

6 Claims, 5 Drawing Sheets

OTHER PUBLICATIONS

A.A. Priplata et al. "Vibrating insoles and balance control in elderly people" *The lancet* Oct. 2003: vol. 362 pp. 1123-1124.

S. Bar-Haim et al. "Random perturbation: A potential aid in treatment of children with cerebral palsy" *Disability & Rehabilitation* Sep. 2007; pp. 1-9.

Kurz et al. "An artificial neural network that utilizes hip joint actuations to control bifurcations and chaos in a passive dynamic bipedal walking model" *Biological Cybernetics*. Jul. 2005; vol. 93: 213-221.

Patton et al. "Evaluation of robotic training forces that either enhance or reduce error in chronic hemiparetic stoke survivors" *Experimental brain research 2006*; vol. 168: 368-383.

Bar-Haim Simona. "Random stimuli strategy in correction of motor control in children with cerebral palsy". *Thesis submitted for the degree of Doctor of Philosophy*. Submitted to the Ben-Gurion University of the Negev, Beer-Sheva. 2005.

\* cited by examiner

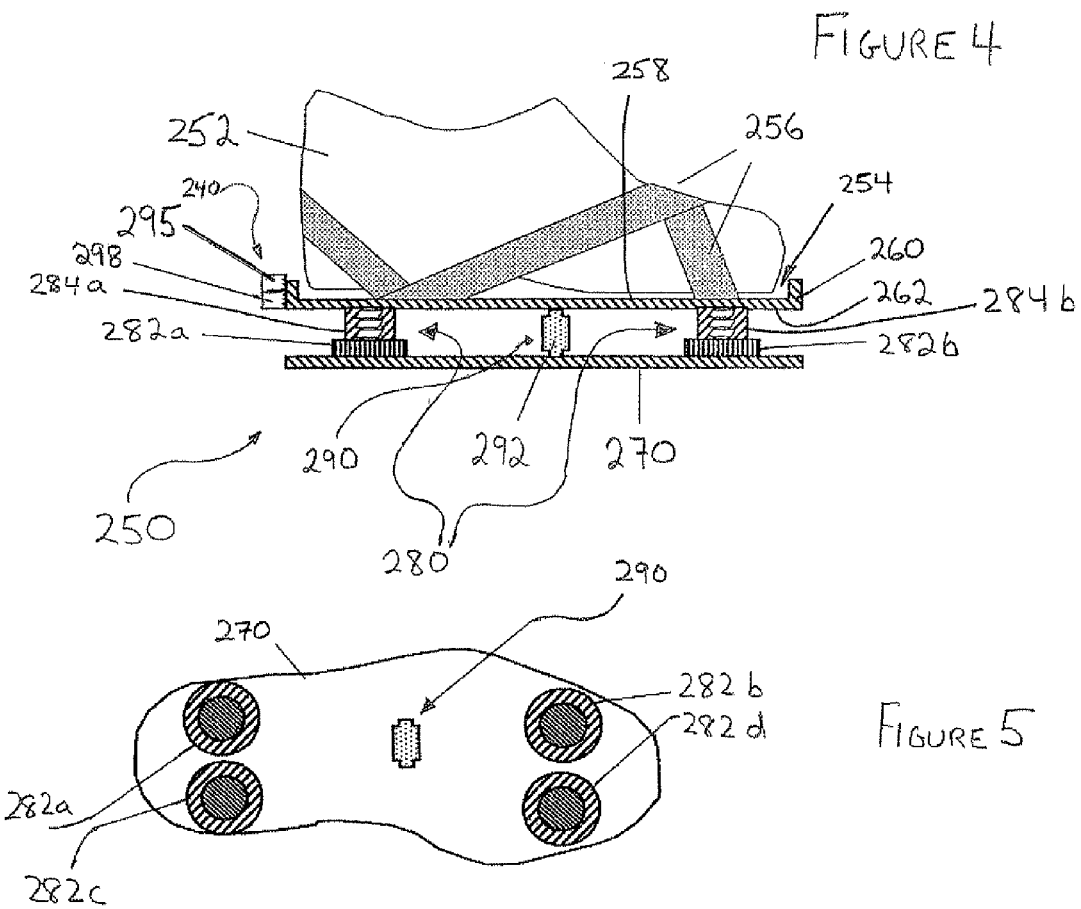
FIGURE 4
FIGURE 5
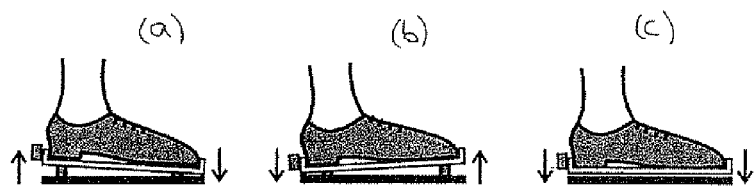
FIGURE 6
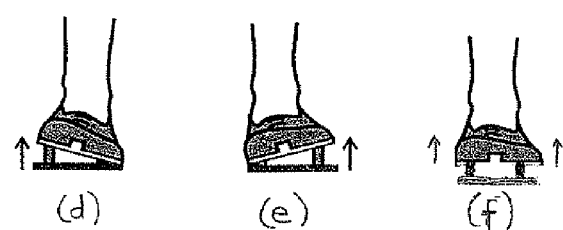

DEVICE AND METHOD FOR IMPROVING HUMAN MOTOR FUNCTION

This application draws priority from U.S. Provisional Patent Application Ser. No. 60/873,296, filed Dec. 7, 2006.

FIELD AND BACKGROUND OF THE INVENTION

The present invention relates to the improvement of motor function and locomotion in humans, and, more particularly, to a method and device for improving such motor function and locomotion by means of random change to the stance angle of a user during gait.

Various methods and devices have been developed in different medical fields for inducing changes in pathological stable patterns (stable attractors). For example, attempts have been made to control epileptic brain seizures by waiting for the system to approach an unstable point from the stable base. A minimal intervention is then required to bring the system back to stability (S. J. Schiff et al., Nature 1994; 370:615-20).

In the control of cardiac arrhythmia, A. Garfinkel et al. (Science 1992; 257:1230-5) developed a method called "proportional perturbation feedback", in which the system state point is perturbed so as to move the state point toward the stable manifold.

Studies have demonstrated that adding noise by applying low-level random vibrations to the feet can significantly reduce the postural sway during quiet standing in the elderly, patients with diabetes, and stroke subjects. This is based on a phenomenon known as stochastic resonance (A. A. Priplata et al., Annals of Neurology 2006; 59: 4-12). A number of studies have investigated the processes involved in motor adaptation by exposing subjects to specific perturbations and quantifying the changes in their responses over time. These perturbations were usually imposed during the performance of a task in a fixed or random fashion.

United States Patent Publication No. 20040173220 to Harry et al. discloses a method and wearable system for enhancing human balance and gait and preventing foot injury through neurological stimulation of the foot and the ankle. Subthreshold stimulation for neurosensory enhancement is provided via electrodes or vibrational actuators, or combination thereof, disposed in or on a wearable a platform, such as an insole, sock shoe, removable shoe insert, or applied without the support of a platform, to the skin surface of an individual. Suprathreshold stimulation for therapeutic purposes, such as improving blood flow, is also provided by the vibrational actuators. The actuators and electrodes are driven by bias signals generated by a bias signal generator that is coupled to a controller. The signal generator under the control of the controller is adapted to generate a non-deterministic random signal, a repetitive pattern or series of patterns.

The merits and efficacies of the above-described devices and methods notwithstanding, it would be highly advantageous to have a method and device for improving motor function and locomotion of a user.

SUMMARY OF THE INVENTION

According to the teachings of the present invention there is provided a system for improving locomotion and motor function of a human user, by changing an inclination or height of a stance surface of a device for donning on a leg of the user during walking, the system including: (A) a device including: (a) a platform having, on a top side, a receptacle adapted to receive at least a portion of a bottom of a shoe or foot of the user; (b) a securing mechanism, associated with the receptacle, to secure the shoe or foot in the receptacle; (c) at least one sole adapted to contact a ground surface; (d) at least one mechanism, at least partially disposed between, and operatively associated with, the sole and a bottom side of the platform, each of the at least one mechanism including: (i) a motor, operatively connected to a power source, and (ii) at least one thrusting element, mechanically associated with, and activated by, the motor, the thrusting element adapted to move, when in thrusting mode, between the sole and the platform so as to apply an upward force against the bottom side of the platform, thereby changing a height of at least a portion of the platform with respect to the sole; (B) a sensor device including at least one sensor adapted to associate with a lower limb of the user, and to produce a data signal related to locomotion of the user, and (C) a microprocessor, operatively connected to the at least one sensor and to the motor, the microprocessor adapted to: (i) receive locomotion information based on the data signal; (ii) process the locomotion information to make a determination of a locomotion phase of the user, and (iii) control a timing of the at least one mechanism, based on the determination, so as to effect the changing of the height during a swing phase of the locomotion of the user.

According to further features in the described preferred embodiments, the at least one thrusting element is adapted to apply the upward force against the bottom side of the platform, so as to change the height of less than an entirety of the platform, with respect to the sole, such that during a particular one of the swing phase, an angle of the platform with respect to the sole is changed.

According to still further features in the described preferred embodiments, the at least one thrusting element is adapted to apply the upward force against the bottom side of the platform, so as to change the height in a varying fashion with respect to the sole, during a particular one of the swing phase, such that an angle of the platform with respect to the sole is changed.

According to still further features in the described preferred embodiments, the at least one thrusting element is adapted to apply the upward force against the bottom side of the platform, so as to change the height of substantially an entirety of the platform, with respect to the sole, such that during a particular one of the swing phase, an angle of the platform with respect to the sole remains unchanged.

According to still further features in the described preferred embodiments, the at least one thrusting element is adapted to apply the upward force against the bottom side of the platform, so as to change the height of the platform, with respect to the sole, such that during a particular one of the swing phase, a heel of the platform is raised with respect to a toe of the platform.

According to still further features in the described preferred embodiments, the at least one thrusting element is adapted to apply the upward force against the bottom side of the platform, so as to change the height of the platform, with respect to the sole, such that during a particular one of the swing phase, a toe of the platform is raised with respect to a heel of the platform.

According to still further features in the described preferred embodiments, the at least one thrusting element is adapted to apply the upward force against the bottom side of the platform, so as to change the height of the platform, with respect to the sole, such that during a particular one of the swing phase, the platform is angled with respect to the sole at least at least along a lateral dimension of the platform.

According to still further features in the described preferred embodiments, the platform can be angled with respect to the sole along the lateral dimension of the platforms such that an exterior side of the platform is raised with respect to an interior side of the platform.

According to still further features in the described preferred embodiments, the platform can be angled with respect to the sole along the lateral dimension of the platform, such that an interior side of the platform is raised with respect to an exterior side of the platform.

According to still further features in the described preferred embodiments, the at least one thrusting element is adapted to apply the upward force against the bottom side of the platform, so as to change the height in a varying fashion with respect to the sole, during a particular one of the swing phase, such that an angle of the platform with respect to the sole is changed, and wherein the angle is diagonal to a lateral dimension of the platform and to a front-to-back dimension of the platform.

According to still further features in the described preferred embodiments, the at least one thrusting element is a plurality of thrusting elements.

According to still further features in the described preferred embodiments, the microprocessor is further adapted to effect a series of changes in the height of at least a portion of the platform according to a predetermined pattern.

According to still further features in the described preferred embodiments, the microprocessor is further adapted to effect a series of changes in the height of at least a portion of the platform according to a predetermined pattern, the predetermined pattern corresponding to a training program matched to a level of motor function of the user.

According to another aspect of the present invention there is provided a system for improving locomotion and motor function of a human user, by randomly changing an inclination or height of a stance surface of a device for donning on a leg of the user during walking, the system including: (A) a device including: (a) a platform having, on a top side, a receptacle adapted to receive at least a bottom of a shoe or foot of the user; (b) a securing mechanism, associated with the receptacle, to secure the shoe or foot in the receptacle; (c) at least one sole adapted to contact a ground surface; (d) at least one mechanism, at least partially disposed between, and operatively associated with, the sole and a bottom side of the platform, each of the at least one mechanism including: (i) a motor, operatively connected to a power source, and (ii) at least one thrusting element, mechanically associated with, and activated by, the motor, the thrusting element adapted to move, when in thrusting mode, between the sole and the platform so as to apply an upward force against the bottom side of the platform, thereby changing a height of at least a portion of the platform with respect to the sole; (B) a sensor device including at least one sensor adapted to associate with a lower limb of the user, and to produce a data signal related to locomotion of the user, and (C) a microprocessor, operatively connected to the at least one sensor and to the motor, the microprocessor adapted to: (i) receive locomotion information based on the data signal; (ii) process the locomotion information to make a determination of a locomotion phase of the user, and (iii) control a timing of the at least one mechanism, based on the determination, so as to effect the changing of the height during a swing phase of the locomotion of the user, and (iv) control the at least one mechanism so as to randomly change the height of the at least a portion of the platform.

According to further features in the described preferred embodiments, the at least one thrusting element is adapted to apply the upward force against the bottom side of the platform, so as to change the height in a varying fashion with respect to the sole, during a particular one of the swing phase, such that an angle of the platform with respect to the sole is changed.

According to still further features in the described preferred embodiments, the microprocessor is further adapted to control the at least one mechanism so as to make directional changes in the angle.

According to still further features in the described preferred embodiments, the microprocessor is further adapted to make control the at least one mechanism so as to make quantitative changes in the angle.

According to still further features in the described preferred embodiments, the microprocessor is further adapted to control the at least one mechanism so as to make both directional changes in the angle and quantitative changes in the angle.

According to yet another aspect of the present invention there is provided a method of improving locomotion and motor function of a human user, by changing an inclination or height of a stance surface of a device for donning on a leg of the user during walking, the method including the steps of: (a) providing a system including: (i) a platform having, on a top side, a receptacle adapted to receive at least a bottom of a shoe or foot of the user; (ii) at least one sole adapted to contact a ground surface; (iii) at least one mechanism, at least partially disposed between, and operatively associated with, the sole and a bottom side of the platform, each of the at least one mechanism including: (A) a motor, operatively connected to a power source, and (B) a thrusting element, mechanically associated with, and activated by, the motor, the thrusting element adapted such that when in thrusting mode, the element moves between the sole and the platform so as to apply an upward force against the bottom side of the platform, thereby changing a height of at least a portion of the platform with respect to the sole, (iv) a sensor device including at least one sensor adapted to associate with a lower limb of the user, and to produce a data signal related to the locomotion of the user; (v) a microprocessor, operatively connected to the at least one sensor and to the motor, (b) securing the shoe or foot of the user in the receptacle; (c) initiating the locomotion of the user; (d) receiving, by the microprocessor, locomotion information based on the data signal; (e) processing the locomotion information to make a determination of a locomotion phase of the user; (f) controlling a timing of the at least one mechanism, based on the determination, so as to effect the changing of the height during a swing phase of the locomotion of the user.

According to further features in the described preferred embodiments, the method further includes the step of: (g) randomly changing the height during the swing phase of the locomotion of the user.

According to still further features in the described preferred embodiments, the height is changed so as to change a stance angle of a foot of the user.

According to yet another aspect of the present invention there is provided a method of improving locomotion and motor function of a human user, by randomly changing an inclination or height of a stance surface of a device for donning on a leg of the user during walking, the method including the steps of: (a) providing a system including: (i) a platform having, on a top side, a receptacle adapted to receive at least a bottom of a shoe or foot of the user; (ii) at least one sole adapted to contact a ground surface; (iii) at least one mechanism, at least partially disposed between, and operatively associated with, the sole and a bottom side of the platform, each of the at least one mechanism including: (A) a motor, operatively connected to a power source, and (B) a thrusting element, mechanically associated with, and activated by, the motor, the thrusting element adapted such that when in thrusting mode, the element moves between the sole and the platform so as to apply an upward force against the bottom side of the platform, thereby changing a height of at least a portion of the platform with respect to the sole, (iv) a sensor device including at least one sensor adapted to associate with a lower limb of the user, and to produce a data signal related to the locomotion of the user; (v) a microprocessor, operatively connected to the at least one sensor and to the motor, (b) securing the shoe or foot of the user in the receptacle; (c) initiating the locomotion of the user; (d) receiving, by the microprocessor, locomotion information based on the data signal; (e) processing the locomotion information to make a determination of a locomotion phase of the user; (f) controlling a timing of the at least one mechanism, based on the determination, so as to effect the changing of the height during a swing phase of the locomotion of the user, and (g) controlling the at least one mechanism so as to randomly change the at least a portion of the height of the platform.

According to further features in the described preferred embodiments, the at least one mechanism is controlled so as to elicit a spontaneous gait-related response of the user to the stimulus provided by the changing of the height of the platform, thereby improving the motor function.

According to yet another aspect of the present invention there is provided a system for improving locomotion and motor function of a human user, by randomly changing an inclination or height of a stance surface of a device for donning on a leg of the user during walking, the system including: (A) a device including: (a) a platform having, on a top side, a receptacle adapted to receive at least a bottom of a shoe or foot of the user; (b) at least one sole adapted to contact a ground surface; (c) at least one mechanism, at least partially disposed between, and operatively associated with, the sole and a bottom side of the platform, each of the at least one mechanism including: (i) a motor, operatively connected to a power source, and (ii) at least one thrusting element, mechanically associated with, and activated by, the motor, the thrusting element adapted to move, when in thrusting mode, between the sole and the platform so as to apply an upward force against the bottom side of the platform, thereby changing a height of at least a portion of the platform with respect to the sole; (B) a sensor device including at least one sensor adapted to associate with a lower limb of the user, and to produce a data signal related to locomotion or to standing posture of the user, and (C) a microprocessor, operatively connected to the at least one sensor and to the motor, the microprocessor adapted to: (i) receive information based on the data signal, and (ii) process the information to make a determination of motor distortion of the user.

According to still further features in the described preferred embodiments, the microprocessor is further adapted to: (iii) determine a form of therapy for the user, based on said determination of motor distortion.

According to still further features in the described preferred embodiments, the microprocessor is further adapted to: (iv) implement the form of therapy for the user, based on said determination of motor distortion.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like elements.

In the drawings:

FIG. 4 is a schematic side view of a shoe inserted into an exemplary embodiment of the inventive device;

FIG. 5 is a schematic bottom view of the embodiment provided in FIG. 4;

FIG. 6 provides three schematic side views and three schematic frontal views of a shoed foot inserted into the inventive device provided in FIG. 4;

FIG. 7 is a schematic depiction of the locomotion of a patient wearing the inventive device provided in FIG. 4, wherein:

FIG. 7A shows random changes or perturbations in the platform angle that transpire during the swing phase;

FIG. 7B shows the resulting locomotion of the patient, and more specifically, the reaction of the patient to such perturbations during each successive stance phase.

DESCRIPTION OF THE PREFERRED EMBODIMENTS

Figure 1:
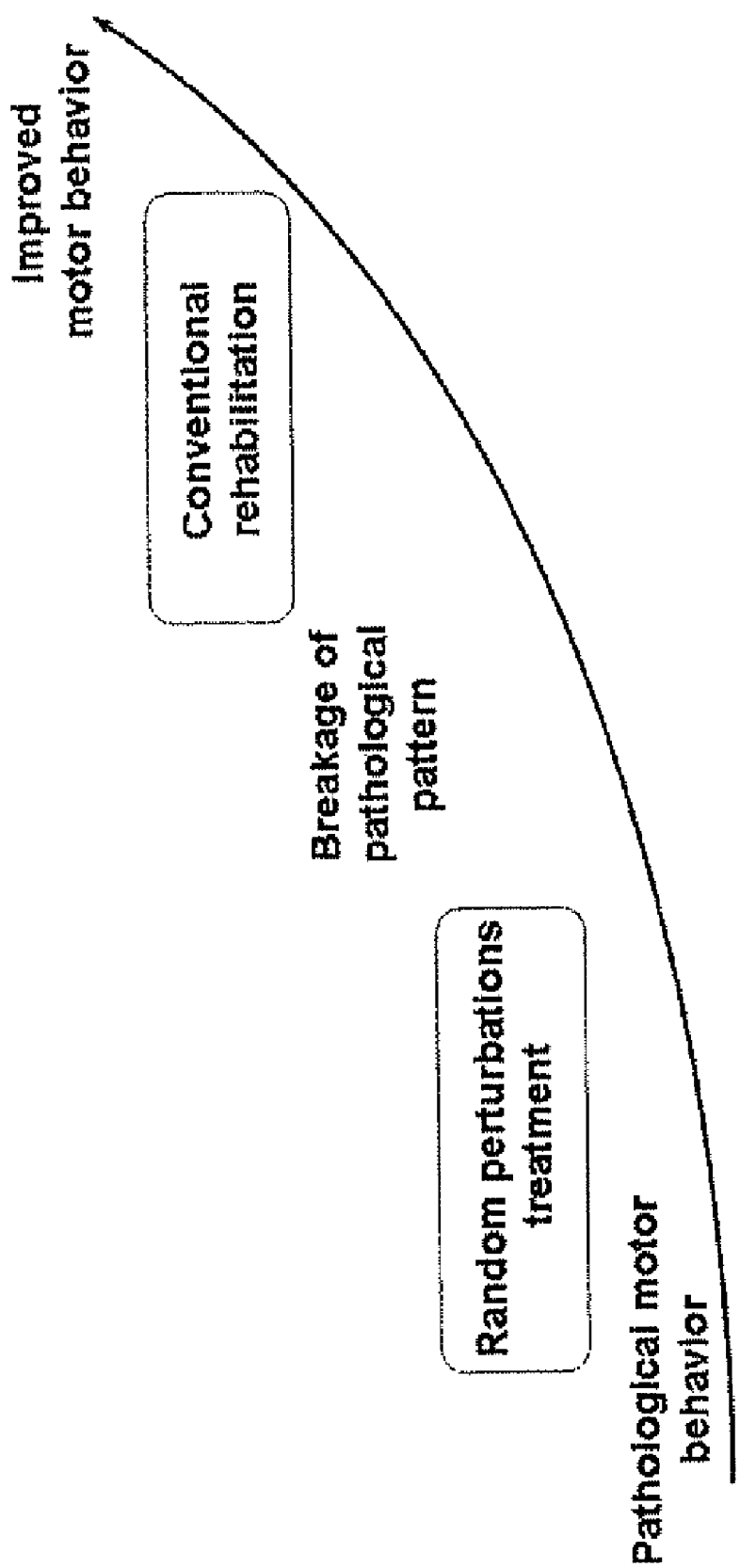
FIG. 1 is a block diagram of one embodiment of the inventive treatment method, in which the inventive, active random perturbation treatment is succeeded by conventional therapy.

One aspect of the present invention is a method and device for improving motor function and locomotion by means of a perturbation applied to a foot apparatus, so as to change, preferably randomly, the stance angle or stance height for a foot of the user, during gait.

The principles and operation of the method and device according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As used herein in the specification and in the claims section that follows, the terms "random" and "chaotic", with respect to a perturbation and the like, are used substantially interchangeably to refer to a perturbation that is of an unpredictable nature with respect to the perception of the patient using the device.

The present invention is based on motor learning and problem solving as a reaction to random perturbations. In normal humans, 32 muscles work in synergy during gait in order to maintain balance. Repetitive continuation of movement has been found to be much more effective for the therapeutic intervention because such intervention involves active problem solving by the central nervous system and also requires multilevel natural biofeedback loops. By sharp contrast, a passive movement of limbs mostly involves the afferent one-way pathways for information gathering, but fails to stimulate, or at least to appreciably stimulate, the usage of this information.

Various aspects of the present invention incorporate a "dynamic systems" approach in conceptualizing the control of voluntary movements, and stability is an important movement characteristic within this approach. Stability of movements may be viewed as a positive feature that allows motor goals to be achieved under conditions of unexpected changes in environment. However, high stability also acts against adaptive changes in movement patterns and can be viewed as inhibiting movement flexibility and thus, optimal performance.

Organization of motor functions in typical and atypical motor behaviors is a dynamic process. Accordingly, the individual and the environment can be considered as one complex dynamic system, connected interactively by afferent pathways conveying sensory information about the environment to the individual, and efferent pathways effecting changes within the environment.

Under the regime of these multiple interconnections, the system tends to attain stable states, called "attractors" that are interpreted as preferred behavioral states.

The motor behavior of persons with movement disorders is an optimal outcome, based on individual constraints such as spasticity, high level of co-activation of agonist and antagonist muscles at a joint and high energy cost. Therefore, some of this motor behavior can be described as "hard-wired," "stereotyped" or "obligatory." Stereotypy and resistance to change characterize these atypical movement patterns and they can be considered to have a "stiff attractor." The consequences of stiff attractors are pathological motor functions, poor repertoire of motor behaviors and functioning difficulties in changeable environments.

When subjects adapt to new external forces, they learn to compensate for these forces by restoring previously learned movements. However, there is evidence that subjects learn to anticipate external forces when the perturbations do not change, or are largely predictable. One aspect of the inventive method involves applying an unexpected random external motion to the foot of the user, during walking, so as to inhibit, or greatly reduce, the counterproductive cycle encountered in known systems and methods, in which the user learns the perturbation scheme, anticipates the next perturbation, and deviates from a normal gait pattern so as to disadvantageously compensate for the anticipated perturbation.

In sharp contrast to the known art, the method and system of the present invention preferably employ random, non-invasive perturbations during active performance of motor tasks so as to loosen highly stable motor behaviors and facilitate motor flexibility and learning in the user. This learning, in contrast to the detrimental learning of the perturbation scheme described above, has a positive effect on motor behavior. We have found that random perturbations during active walk or cycling serve to remove the motor control system from its stable "stiff attractor" state and to facilitate improved motor functions.

The incorporation of random perturbations within an intensive physical treatment program could serve to improve the outcomes for various populations having movement disorders and for those prone to falling, including elderly fallers. The populations that may benefit from the present invention may include those having movement and posture disorders that cause activity limitation. Such movement and posture disorders are attributed to non-progressive disturbances that occurred in the developing fetal or infant brain or even in adulthood. These disorders may be found in children with Cerebral Palsy, persons following traumatic brain injury, and in persons with hemiplegia as a result of a cerebro-vascular incident. In addition, patients prone to falling of falling can gain stability in their balance and/or locomotion.

Referring now to the drawings, FIG. 1 is a block diagram of one embodiment of the inventive treatment method, in which the inventive, active random perturbation treatment is succeeded by conventional therapy, after tangible, measurable results from the inventive treatment method become evident. As a result of the preferably random stimuli, and the reaction thereto, a patient or user enters a transient state having increased variability or additional degrees of freedom. This state enables enhanced progress from subsequently-applied conventional therapies.

After pathological motor behavior is identified, the user undergoes an active perturbation treatment of the present invention. This treatment will be described in greater detail hereinbelow. Once it is evident that the pathological pattern has been broken, a conventional rehabilitation process is initiated, which typically leads to further improvements in the motor behavior. It must be emphasized that these further improvements in the motor behavior are largely attributable to the active perturbation treatment that preceded the conventional rehabilitation process.

Figure 2:
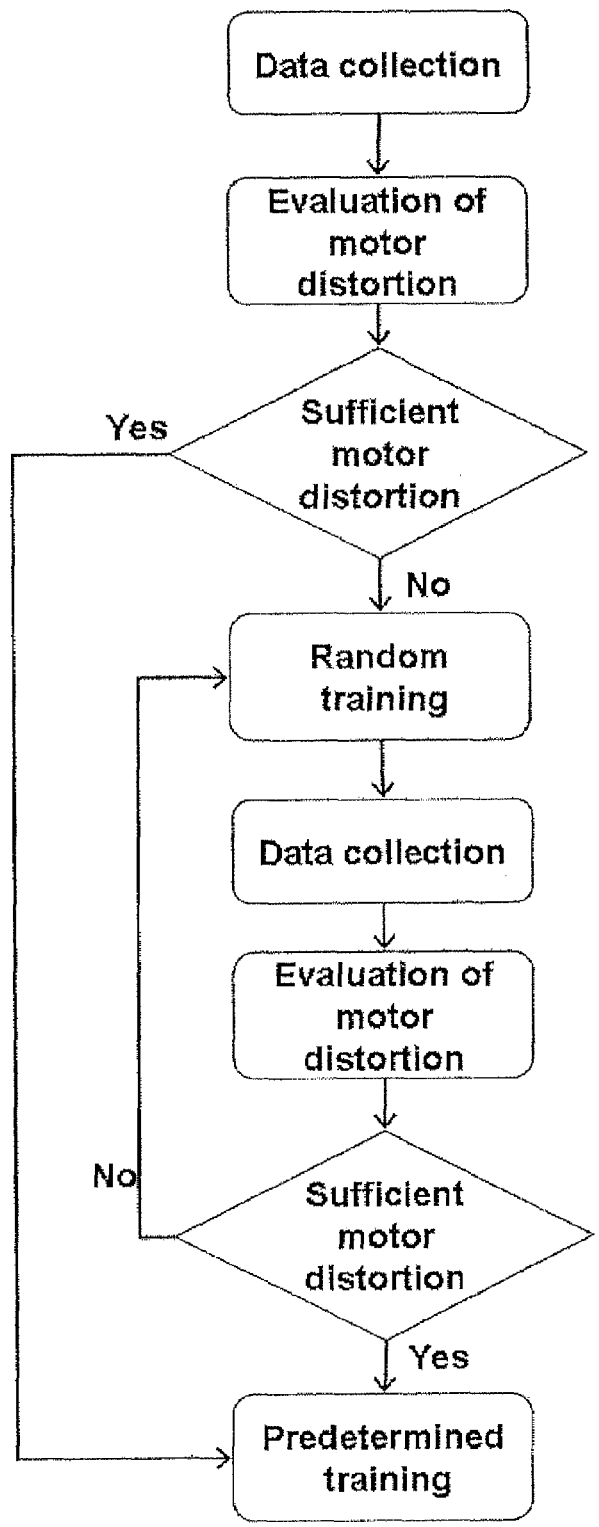
FIG. 2 is a schematic logical flow diagram according to another embodiment of the inventive treatment method, showing the data collection and processing steps performed by the controller.

FIG. 2 is a schematic logical flow diagram according to another embodiment of the inventive treatment method, showing the data collection and processing steps performed by the controller or microprocessor. If the patient has achieved sufficient motor distortion, e.g., above a pre-determined threshold, the patient can progress to conventional therapy, i.e., to a predetermined therapy. If the patient has not achieved sufficient motor distortion, even after undergoing an active perturbation treatment of the present invention, then the patient must begin, or continue, the active perturbation treatment.

The pre-determined threshold may or may not be patient-specific.

Subsequently, motor distortion of the patient is again evaluated. If the patient has achieved sufficient motor distortion, the patient can progress to conventional therapy, as described. If, however, the patient has not yet achieved sufficient motor distortion, the patient continues with the active perturbation treatment, until ultimately, sufficient motor distortion has been achieved.

Data collected by the controller from sensors may include the parameters for order evaluation, like variability parameters such as standard deviation, variance, Poincaré map, and spectral density; or chaos parameters such as fractal dimension, Lyapunov exponent, Hurst exponent, approximate entropy, or correlation dimension.

After evaluating the degree of motor distortion, the controller decides, or recommends to the therapist, whether a patient can progress to conventional therapy or requires additional random perturbation training.

One aspect of the method of the present invention is partly based on a "dynamic systems" approach in conceptualizing the control of voluntary movements, consequently improving motor functions, human movement and posture through random perturbation. The application of the method needs random or deliberate changes in the slope or height of the surface with which a patient is interacting while actively performing a task. The mode of changes (rate of changes, slope, slope direction, height; in cycling: resistance, crank radius, pedal position along the axis, asynchronization, pattern and number of variables) are individual for each patient according to his pathology and progress during the treatment. The changes for each foot are independent. During the treatment session, the patient is made to perform active movements (i.e. steps, walking, stair climbing, cycling revolutions, etc.), reacting to random changes in stance height or stance angle made by the device.

Preferably, the inventive method and device can enable (a) a non-deterministic, random mode; (b) a predetermined mode in which a pattern is repeated, or both modes. The mode of operation may be selected via the associated computer.

Figure 3:
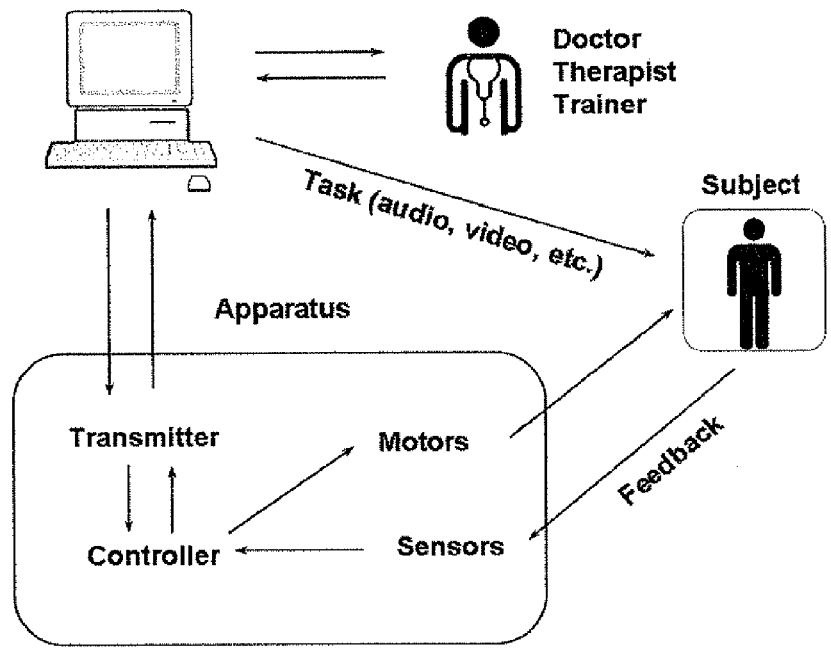
FIG. 3 is a schematic diagram showing the main components of one embodiment of the inventive system, along with various interactions within the system, and between the system, the patient, and the physician or trainer.

FIG. 3 is a schematic diagram showing the main components of one embodiment of the inventive system, along with various interactions (some of which are further elaborated hereinbelow) within the system, and between the system, the patient, and the physician, therapist, or trainer. Inventive system 200 includes an inventive apparatus or device 250, and a computer 210 such as a personal computer (PC).

FIG. 4 is a schematic side view of a shoe 252 inserted into an exemplary embodiment of inventive device 250. Device 250 preferably includes a receptacle 254 adapted to receive at least a portion of shoe 252, and a securing mechanism such as strap mechanism 256, associated with receptacle 254, to secure and unsecure shoe 252, or a foot of the user, on a stance surface 258 in receptacle 254.

Device 250 is equipped with a platform 260 or other means adapted to support shoe 252. Device 250 further includes at least one sole 270 adapted to contact a ground surface, and a stance adjustment mechanism 280, which is at least partially disposed between, and operatively associated with, sole 270 and a bottom side 262 of platform 260.

Stance adjustment mechanism 280 includes a motor 282, operatively connected to a power source (not shown), and at least one thrusting element such as thrusting elements 284a and 284b, which are mechanically associated with, and activated by, motors 282a and 282b, respectively. Thrusting elements 284a and 284b are adapted to move, when in thrusting mode, between sole 270 and platform 260 so as to apply a force, in this case an upward force, against bottom side 262 of platform 260. Thus, when in thrusting mode, thrusting elements 284a and 284b change a height of at least a portion of platform 260 with respect to sole 270.

It will be appreciated that stance adjustment mechanism 280 is exemplary, and that many alternative mechanisms and modifications could be contemplated by one skilled in the art. For example, an eccentric or asymmetric rotating element (such as a disk or wheel) could be used as one or more thrusting element. Also, the thrusting elements could extend and contract in a screw-type motion, or as telescopic arms.

Stance adjustment mechanism 280 is preferably adapted to provide a variety of inclinations or heights of stance surface 258, as will be elaborated hereinbelow.

Device 250 further includes, or is at least operatively associated with, at least one sensor device 290 having at least one sensor 292 designed to measure a gait parameter such as weight, pressure, an angle of rotation associated with a lower limb of the user, etc., and to produce a data signal related to locomotion. Thus, sensor device 290 may include be a pressure sensor, an accelerometer, a gyroscope, a magnetic field sensor, a heel switch, or other sensors. In FIG. 4, sensor device 290 is a weight or pressure sensor disposed between sole 270 and platform 260.

From the data signal provided by sensor device 290, the locomotion phase of the user can be determined (e.g., by the controller). In one preferred embodiment, swing phase, stance phase, or both may be determined from the data signal. The methods of making this determination will be readily apparent to those skilled in the art.

Stance adjustment mechanism 280 is controlled by a controller 298 (e.g., a microprocessor). Controller 298 may be disposed in, or attached to, device 250, for example, as part of an electronic unit 240 attached to platform 260. It will be appreciated, however, that controller 298, while being operatively associated with stance adjustment mechanism 280, may be physically disposed elsewhere, such as in a separate control unit. Computer 210 may be adapted to function as controller 298. Some of the functions of controller 298 have described with regard to FIG. 2, others are elaborated hereinbelow.

Electronic unit 240 may include a transmitter or transceiver 295, for maintaining at least one-way communication, and preferably two-way communication, with an external device such as computer 210 provided in FIG. 3.

It will be evident to those skilled in the art that shoe 252 may be a shoe of the user, or a stationary boot in which the shoe or foot of the user is inserted.

It will also be evident to those skilled in the art that device 250 can be used, or adapted to be used, in conjunction with a pedal of a bicycle and the like.

FIG. 5 is a schematic cross-sectional representation of the embodiment provided in FIG. 4. From this view are evident sensor device 290 and motors 282a and 282b, shown in FIG. 4, and motors 282c and 282d, which were not viewable from that side view. A projection of sole 270 is provided to facilitate understanding of the figure.

FIG. 6 provides three schematic side views and three schematic frontal views of a shoed foot inserted into the inventive device provided in FIG. 4. These views display a variety of stance angles being applied to a foot of the user. Referring now to side views (a)-(c), side view (a) shows stance adjustment mechanism 280 (shown in FIG. 4) acting to lift the rear end of platform 260, and consequently, the heel of shoe 252, relative to the front end of platform 260, and the toe of shoe 252. Thus, the action of mechanism 280 effects plantar flexion on the foot of the user inserted in 252.

In view (b), stance adjustment mechanism 280 has acted to lift the front end of platform 260, and consequently, the toe of shoe 252, relative to the rear end of platform 260, and the heel of shoe 252. In this case, the action of mechanism 280 effects dorsiflexion on the foot of the user inserted in 252.

In view (c), stance adjustment mechanism 280 is in a neutral mode, in which the thrusting mechanism is relaxed, such that the foot assumes a substantially normal posture.

Referring now to frontal views (d)-(f), frontal view (d) shows stance adjustment mechanism 280 (shown in FIG. 4) acting to lift an inner side (i.e., the instep side) of platform 260, and consequently, the instep of shoe 252, relative to the outer side of platform 260, and the outer side of shoe 252. Thus, the action of mechanism 280 effects supination on the foot of the user inserted in 252.

In view (e), stance adjustment mechanism 280 has acted to lift the outer side of platform 260, and consequently, the outer side of shoe 252, relative to the inner side of platform 260, and the instep side of shoe 252. Thus, the action of mechanism 280 effects pronation on the foot of the user inserted in 252.

In view (f), stance adjustment mechanism 280 has acted to evenly lift the platform 260, such that the foot has been evenly raised with respect to the normal posture. Such an evenly-raised posture may be useful in effecting therapeutic stance perturbations in accordance with the present invention.

Thus, there are 5 basic stance deviations from the normal posture, that may be described as toe up, heel up, instep up, instep down, and platform up. The degree of inclination, or degree of elevating the platform, may be substantially continuous. Alternatively, there may be a finite number of positions. For example, each basic stance deviation may have 3 discrete angles, corresponding to light, moderate, and extreme stance deviations, and the elevation of the platform ("platform up") may also have 3 discrete levels. In this exemplary case, there are 15 positions of the device that are controlled by the controller at random, or in a pre-determined pattern (e.g., based on specific patient parameters).

Thus, mechanism 280 and the controller of mechanism 280 may be designed to provide several degrees of freedom to the changing of the height of platform 260. For example, each one of thrusting elements 284a-284d could elevate portions of platform 260 to three or even four different heights. Consequently, the inventive device and method can effect a substantially infinite number of directions of inclination, e.g., various diagonal inclinations such as such as "toe and instep up", "heel and instep up". The diagonal inclinations may be weighted, to favor a particular stance direction. Similarly, the controller, the stance adjustment mechanism (such as mechanism 280) and the thrusting elements thereof can be adapted to provide an infinite number of degrees of inclination.

Figure 7:
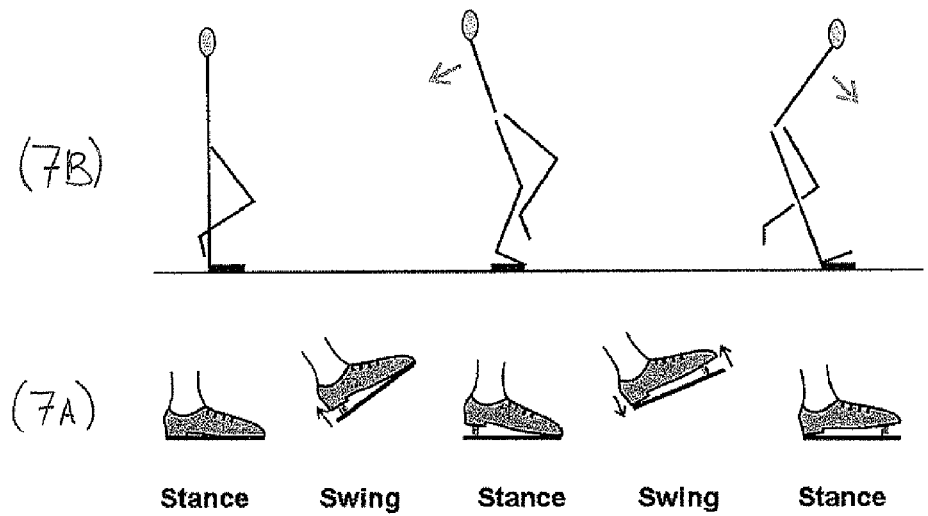

FIG. 7 is a schematic depiction of the locomotion of a patient or user wearing the inventive device such as the device provided in FIG. 4, wherein: FIG. 7A shows (preferably random) changes or perturbations in the platform angle that transpire during the swing phase, and FIG. 7B shows the resulting locomotion of the patient, and more specifically, the reaction of the patient to such perturbations during each successive stance phase. The arrows in FIG. 7B indicate the patient's natural reaction to the perturbation stimuli.

Figure 8:
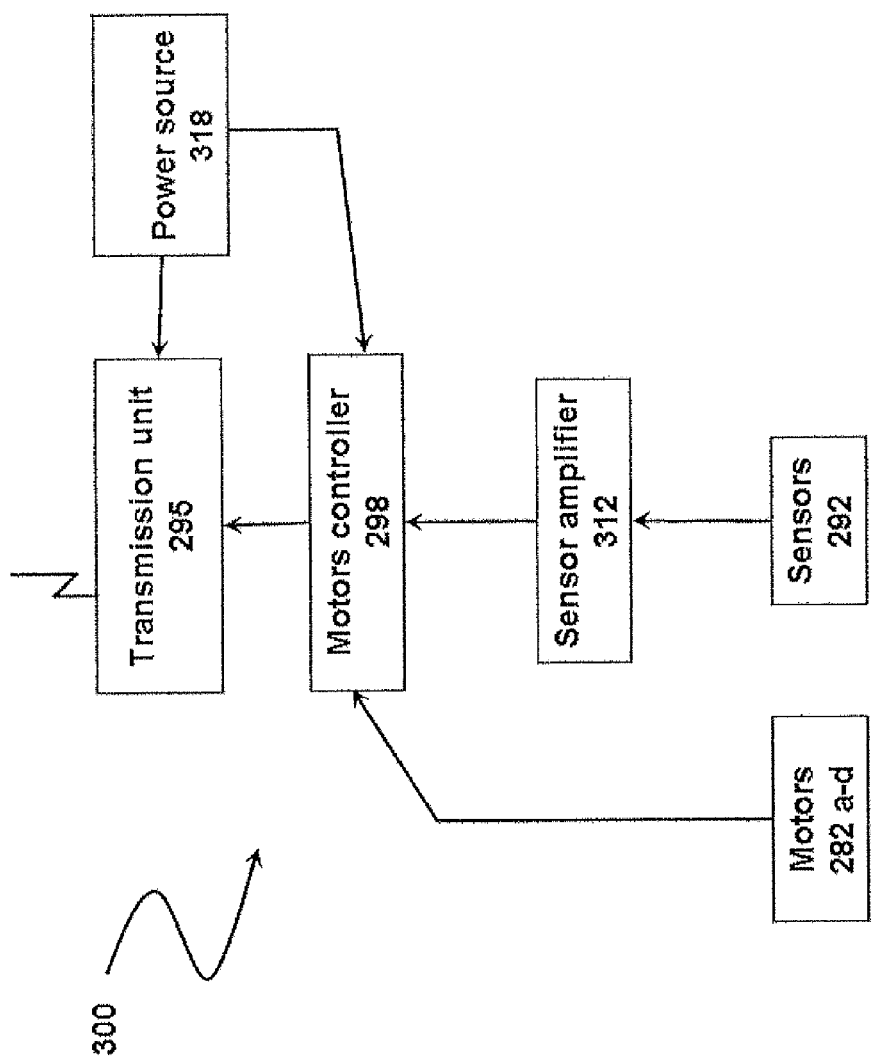
FIG. 8 is a schematic block diagram of an exemplary embodiment of an electronics system associated with, and typically at least partially disposed within, the device of the present invention.

FIG. 8 is a schematic block diagram of an exemplary embodiment of an electronics system 300 associated with, and typically disposed within, device 250 of the present invention.

The electronic components of electronics system 300 include a motor (or motors) controller 298, which may be a microprocessor of various suitable types known to those skilled in the art. Directly electrically connected to controller 298 are two (by way of example) motors, a yaw motor 304 and a pitch motor 306, which may be driven by controller 298 discretely or simultaneously. A least one sensor 308, which generates an electrical signal that correlates with pressure, acceleration, etc., may be electrically connected to controller 298 via a sensor signal amplifier 312, or may be electrically connected to controller 298 in a direct fashion. A modem 316, which may be directly connected to controller 298, provides bi-directional connection with a computer such as a personal computer (PC), shown in FIG. 3, or some other device having a central processing unit (CPU). The electrical power to the various electronic components is provided by a power source 318, which is preferably connected directly to controller 298.

All the stance position changes are performed during the swing phase of gait. Typically, these position changes are performed entirely during the swing phase of gait. The gait or locomotion phase is determined by controller 298, based on the readings from the sensor, e.g., sensor 308.

Controller 298 may also manage the connection between the inventive device and the computer associated therewith.

The power source for the device is a battery or electricity generator powered by electrical generator driven by walking human or accumulator chargeable from a mains socket or generator. An external power source (i.e., mains socket or USB connection) can be used for a stationary device or for the device attached to a pedal of stationary cycling-ergometer. The connection between the device and the computer may be wired or wireless and enables the operation and adjustment of the mode of performance of the device and for data collection for feedback-loop building or for further storage, or for functional performance monitoring, and diagnostics.

In a preferred embodiment of the present invention, the system features a predetermined or embedded training program, which may be patient-specific. In this program, various restrictions on the actions of the system may be made, including restrictions on the platform position, restrictions on the range of inclination, and restrictions of tasks to the user that are assigned by the system.

For example, for a patient assessed as having a poor level of performance, the level of impairment is defined by the system as severe, the chosen training program will include the minimal ranges or levels of inclination and no complex tasks, like "walk backwards". As another example, a professional may restrict the device action to one foot only, due to orthopedic symptoms in the other foot.

The controller may determine or assess (or update) the level of impairment of motor function of a user based on information obtained from the sensor. The level of impairment may also be entered or updated manually.

The software of the present invention preferably has at least two interfaces: an interface for use by professionals (doctors, therapists, etc.), in the training, programming, follow-up and diagnostics; and a more simple and more limited "patient's" interface for self-use of the system.

The system is preferably programmed such that a subject or patient receives an auditory or visual command from the computer to perform a task using the inventive device. Examples of a task are: to walk or cycle toward pointed direction; to walk or cycle with a given rhythm; to walk or cycle at a given velocity; to perform a sequence of single steps, each one in a given direction, etc. According to the success of the performance and subject to various predetermined restrictions, the computer adjusts (or allows the patient or physician or trainer to adjust) the mode. Feedback may be provided in the following ways: personalized messages, images, video, and/or sound. The patient's motivation may be stimulated by scoring systems, speeds, time trajectory deviations, accuracy of target achievements, rhythms, etc. The data of the task performance is recorded and may be graphically represented.

The computer program also includes a database of subjects, the results of previous sessions (success rate of a patient), posture and gait parameters (or cycling parameters of a subject) for follow up and diagnostics, and a report generator. The parameters for diagnostics and follow-up may include gait and equilibrium analysis, and the completion of a task.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for improving locomotion and motor function of a human user, by changing an inclination or height of a stance surface of a device for donning on a leg of the user during walking, the system comprising:
   (A) a device including:
      (a) a platform having, on a top side, a receptacle adapted to receive at least a portion of a bottom of a shoe or foot of the user;
      (b) a securing mechanism, associated with said receptacle, to secure said shoe or foot in said receptacle;
      (c) at least one sole adapted for a direct contact with a ground surface; and
      (d) at least one mechanism, at least partially disposed between, and operatively associated with, said sole and a bottom side of said platform, each of said at least one mechanism including:
         (i) a motor, operatively connected to a power source, and
         (ii) at least one thrusting element, mechanically associated with, and activated by, said motor, said thrusting element adapted
            (I) to move, when in thrusting mode, between said sole and said platform so as to apply an upward force against said bottom side of said platform, thereby changing a height of at least a portion of said platform with respect to said sole; and
            (II) to apply said upward force against said bottom side of said platform, so as to change said height of said platform, with respect to said sole, such that during a swing phase, said platform is angled with respect to said sole at least along a lateral dimension of said platform;
   (B) a sensor device including at least one sensor adapted to associate with a lower limb of the user for sensing locomotion of the user, and to produce a data signal related to the sensed locomotion of the user, and
   (C) a microprocessor operatively connected to said at least one sensor and to said motor, said microprocessor adapted to:
      (i) receive locomotion information based on said data signal;
      (ii) process said locomotion information to make a determination of a locomotion phase of the user, and
      (iii) control a timing of said at least one mechanism, based on said determination, so as to effect said changing of said height during a swing phase of the locomotion of the user.

2. The system of claim 1, wherein said platform is angled with respect to said sole along said lateral dimension of said platform, such that an exterior side of said platform is raised with respect to an interior side of said platform 3. The system of claim 1, wherein said platform is angled with respect to said sole along said lateral dimension of said platform, such that an interior side of said platform is raised with respect to an exterior side of said platform.

4. A system for improving locomotion and motor function of a human user, by randomly changing an inclination or height of a stance surface of a device for donning on a leg of the user during walking, the system comprising:
   (A) a device including:
      (a) a platform having, on a top side, a receptacle adapted to receive at least a bottom of a shoe or foot of the user;
      (b) a securing mechanism, associated with said receptacle, to secure said shoe or foot in said receptacle;
      (c) at least one sole adapted for a direct contact with a ground surface; and
      (d) at least one mechanism, at least partially disposed between, and operatively associated with, said sole and a bottom side of said platform, each of said at least one mechanism including:
         (i) a motor, for operatively connecting to a power source, and
         (ii) at least one thrusting element, mechanically associated with, and activated by, said motor, said thrusting element adapted
            (I) to move, when in thrusting mode, between said sole and said platform so as to apply an upward force against said bottom side of said platform, thereby changing a height of at least a portion of said platform with respect to said sole; and
            (II) to apply said upward force against said bottom side of said platform, so as to change said height of said platform, with respect to said sole, such that during a swing phase, said platform is angled with respect to said sole at least along a lateral dimension of said platform;
   (B) a sensor device including at least one sensor adapted to associate with a lower limb of the user for sensing locomotion of the user, and to produce a data signal related to the sensed locomotion of the user, and
   (C) a microprocessor, operatively connected to said at least one sensor and to said motor, said microprocessor adapted to:
      (i) receive locomotion information based on said data signal;
      (ii) process the sensed locomotion information to make a determination of a locomotion phase of the user, and
      (iii) control a timing of said at least one mechanism, based on said determination, so as to effect said changing of said height during a swing phase of the locomotion of the user, and
      (iv) control said at least one mechanism so as to introduce random changes in said height of said at least a portion of said platform.

5. A method of improving locomotion and motor function of a human user, by changing an inclination or height of a stance surface of a device for donning on a leg of the user during walking, the method comprising the steps of:
   (a) providing a system including:
      (i) a platform having, on a top side, a receptacle adapted to receive at least a bottom of a shoe or foot of the user;
      (ii) at least one sole adapted for a direct contact with a ground surface;
      (iii) at least one mechanism, at least partially disposed between, and operatively associated with, said sole and a bottom side of said platform, each of said at least one mechanism including:
         (A) a motor, for operatively connecting to a power source, and
         (B) a thrusting element, mechanically associated with, and activated by, said motor, said thrusting element adapted such that when in thrusting mode, said element moves between said sole and said platform so as to apply an upward force against said bottom side of said platform, thereby changing a height of at least a portion of said platform with respect to said sole,
  (iv) a sensor device including at least one sensor adapted to associate with a lower limb of the user for sensing locomotion of the user, and to produce a data signal related to the sensed locomotion of the user;
  (v) a microprocessor, operatively connected to said at least one sensor and to said motor,
(b) securing said shoe or foot of the user in said receptacle;
(c) initiating the locomotion of the user;
(d) receiving, by said microprocessor, locomotion information based on said data signal;
(e) processing said locomotion information to make a determination of a locomotion phase of the user;
(f) controlling a timing of said at least one mechanism, based on said determination, so as to effect said changing of said height during a swing phase of the locomotion of the user;
(g) controlling said at least one mechanism by said microprocessor so as to introduce random changes in said at least a portion of said height of said platform; and
(h) controlling said at least one mechanism so as to elicit a spontaneous gait-related response of the user to the stimulus provided by said changing of said height of said platform.

6. A system for improving locomotion and motor function of a human user, by randomly changing an inclination or height of a stance surface of a device for donning on a leg of the user during walking, the system comprising:

(A) a device including:
  (a) a platform having, on a top side, a receptacle adapted to receive at least a bottom of a shoe or foot of the user;
  (b) at least one sole adapted for direct contact with ground surface;
  (c) at least one mechanism, at least partially disposed between, and operatively associated with, said sole and a bottom side of said platform, each of said at least one mechanism including:
    (i) a motor, for operatively connecting to a power source, and
    (ii) at least one thrusting element, mechanically associated with, and activated by, said motor, said thrusting element adapted to move, when in thrusting mode, between said sole and said platform so as to apply an upward force against said bottom side of said platform, thereby changing a height of at least a portion of said platform with respect to said sole;
(B) a sensor device including at least one sensor adapted to associate with a lower limb of the user for sensing locomotion of the user, and to produce a data signal related to the sensed locomotion or to standing posture of the user, and
(C) a microprocessor, operatively connected to said at least one sensor and to said motor, said microprocessor adapted to:
  (i) receive information based on said data signal;
  (ii) process said information to make a determination of motor distortion of the user; and
  (iii) determine a form of therapy for the user, based on said determination of motor distortion.

\* \* \* \* \*